United States Patent [19]

Riechers et al.

[11] Patent Number: 6,049,007
[45] Date of Patent: Apr. 11, 2000

[54] RACEMIZATION OF OPTICALLY ACTIVE AMINES

[75] Inventors: Hartmut Riechers, Neustadt; Joachim Simon, Mannheim; Arthur Höhn, Kirchheim; Andreas Kramer, Freinsheim; Frank Funke; Wolfgang Siegel, both of Limburgerhof; Christoph Nübling, Hassloch, all of Germany

[73] Assignee: BASF Aktiengesellschaft, Ludwigshafen, Germany

[21] Appl. No.: 09/259,042

[22] Filed: Mar. 1, 1999

[30] Foreign Application Priority Data

Feb. 12, 1999 [DE] Germany .............. 199 05 837

[51] Int. Cl.$^7$ ................................. C07C 209/00
[52] U.S. Cl. ............................................... 564/302
[58] Field of Search ................................. 564/302

[56] References Cited

U.S. PATENT DOCUMENTS

| | | | |
|---|---|---|---|
| 3,954,870 | 5/1976 | Fukumaru et al. | 260/570 |
| 4,014,933 | 3/1977 | Boettger et al. | 260/563 |
| 4,096,186 | 6/1978 | Ichikawa et al. | 260/584 |
| 4,990,666 | 2/1991 | Harsy | 564/302 |
| 5,002,922 | 3/1991 | Irgang et al. | 502/331 |
| 5,530,127 | 6/1996 | Reif et al. | 544/106 |
| 5,847,215 | 12/1998 | Ditrich | 564/302 |

FOREIGN PATENT DOCUMENTS

| | | |
|---|---|---|
| 382049 | 8/1990 | European Pat. Off. |
| 514692 | 11/1992 | European Pat. Off. |
| 696572 | 2/1996 | European Pat. Off. |
| 778260 | 6/1997 | European Pat. Off. |
| 1953263 | 2/1972 | Germany . |
| 2851039 | 6/1980 | Germany . |
| 2903589 | 8/1980 | Germany . |
| 19852282 | 11/1998 | Germany . |
| 19859775 | 12/1998 | Germany . |
| 19905838 | 2/1999 | Germany . |
| 6135906 | 10/1992 | Japan . |
| 98/03465 | 1/1998 | WIPO . |

OTHER PUBLICATIONS

Database WPI, Section Ch, Week 7908, Derwent Publications Ltd., London, GB: Class B05, AN 79–14874B, XP002112502 (English abstract of JP 54 005957, Jan. 17, 1979).

Database WPI, Section Ch, Week 9424, Derwent Publications Ltd., London, GB: Class B05, AN 94–197043, XP002112503 (English abstract of JP 06 135906, May 17, 1994).

Database WPI, Section Ch, Week 5821, Derwent AN 98–234725 (JP 10072410; Mar. 17, 1998).

Pat. Abst. of Japan, vol. 12, No. 467 (JP 63185943, Aug. 1, 1988).

Pat. Abst. of Japan, vol. 95, No. 10 (JP 07188120, Jul. 25, 1995).

*Ullmann's Encyclo. of Ind. Chem.*, vol. A2, pp. 4+5.

Primary Examiner—Samuel Barts
Attorney, Agent, or Firm—Keil & Weinkauf

[57] ABSTRACT

A process for the preparation of racemic amines of the formula I

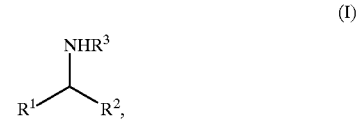

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen, where the radicals can bear substituents selected from the group consisting of alkyl, cycloalkyl, alkoxy, aryloxy, amino, alkylamino and dialkylamino, which comprises simultaneously reacting in situ the corresponding optically active amine I and the secondary alcohol of the formula II and/or the unsymmetrical ketone of the formula III

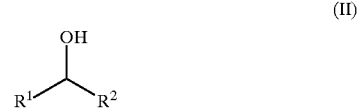

(II)

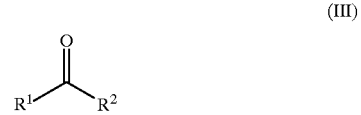

(III)

and the amine of the formula $R^3NH_2$ in the presence of hydrogen and a hydrogenation catalyst or dehydrogenation catalyst at elevated temperature.

12 Claims, No Drawings

RACEMIZATION OF OPTICALLY ACTIVE AMINES

The present invention relates to a process for the preparation of racemic amines of the formula I

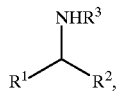

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen (H), where the radicals can bear substituents selected from the group consisting of alkyl, cycloalkyl, alkoxy, aryloxy, amino, alkylamino and dialkylamino.

Racemic amines of the formula I and optically active amines of the formula I are, for example, valuable pharmaceuticals and intermediates for preparing active compounds (cf., for example: DE-A-29 03 589, page 2, lines 17 to 26). Since frequently only one of the two enantiomers (on the basis of the asymmetric carbon atom shown in I) is active or is more active than the other enantiomer, processes are required for the racemization of the less active enantiomer which is obtained, for example, in the resolution of the corresponding racemic amine by known methods, so that the more active enantiomer can again be isolated from the racemized amine by known methods (e.g. resolutuion).

Racemic amines can be prepared according to Ullmann's Encyclopedia of Industrial Chemistry, Vol. A2, pages 4 and 5, VCH Verlagsgesellschaft mbH (1985) by amination of alcohols or by hydrogenating amination of ketones in the presence of hydrogenation or dehydrogenation catalysts at elevated temperature.

Amination processes of this type are described for example in EP-A-382 049, EP-A-514 692, EP-A-696 572 and DE-A-19 53 263.

IN-A-162 213 (Chem. Abstracts 110: 192247v) discloses a process for preparing racemic 2-aminobutanol by treating 1-2-aminobutanol with ammonia in the presence of Rh/Al$_2$O$_3$.

U.S. Pat. No. 4,096,186 describes a process for the racemization of optically active aminoalcohols in which the aminoalcohol is brought into contact with ammonia and hydrogen in the presence of a hydrogenation catalyst which preferably comprises cobalt.

U.S. Pat. No. 4,990,666 discloses a process for the racemization of optically active aminoalcohols in which the aminoalcohol is brought into contact with Raney cobalt in the presence of hydrogen. This patent teaches that high temperatures, e.g. greater than 160° C., reduce the yield of racemic amine.

JP-A-06 135 906 (Derwent Abstract No. 94-197043/24; Chem. Abstracts 121: 179093z) describes a process for the racemization of optically active vicinal primary diamines in the presence of hydrogen and a hydrogenation catalyst such as Raney nickel or Raney cobalt.

DE-A-28 51 039 describes a process for preparing racemic mixtures of optically active 1-arylamines in which the optically active 1-arylamines are treated with hydrogen in the presence of a hydrogenation catalyst, in particular Raney cobalt. DE-A-29 03 589 describes a process for preparing racemic mixtures of optically active amines by treating the optically active amines with hydrogen in the presence of a hydrogenation catalyst, in particular Raney cobalt or Raney nickel, at elevated temperature.

The earlier German application No. 19859775.4 of Dec. 23, 1998, relates to a process for racemizing optically active amines by reacting the optically active amine in the presence of hydrogen and a hydrogenation catalyst or dehydrogenation catalyst at elevated temperature by carrying out the reaction in the gas phase.

It is an object of the present invention to discover an economic process for preparing racemic amines which starts from the corresponding optically active amine and a corresponding alcohol and/or ketone as starting materials, in which process the process product is obtained at high yield based on the starting materials, high space-time yield and a high degree of racemization based on the optically active amine used.

We have found that this object is achieved by a process for the preparation of racemic amines of the formula I

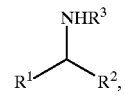

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen (H), where the radicals can bear substituents selected from the group consisting of alkyl, cycloalkyl, alkoxy, aryloxy, amino, alkylamino and dialkylamino, which comprises simultaneously reacting in situ the corresponding optically active amine I (based on the asymmetric carbon shown in I) and the secondary alcohol of the formula II and/or the unsymmetrical ketone of the formula III

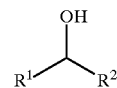

(II)

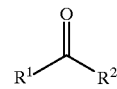

(III)

and the amine of the formula R$^3$NH$_2$ in the presence of hydrogen and a hydrogenation catalyst or dehydrogenation catalyst at elevated temperature.

It is clear here that the radicals $R^1$ and $R^2$ of the alcohol II of the ketone III, of the optically active amine I and of the racemic amine I respectively correspond and the radicals $R^3$ of the amine $R^3$NH$_2$, of the optically active amine I and of the racemic amine I respectively correspond.

The process according to the invention may be illustrated by the following diagram:

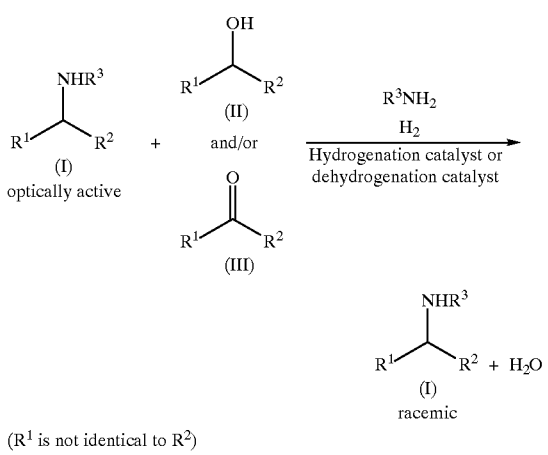

($R^1$ is not identical to $R^2$)

The process according to the invention may be carried out in the liquid phase, or preferably in the gas phase, batchwise, or preferably continuously, as follows, the catalyst preferably being disposed as a fixed bed in the reactor.

The process according to the invention for preparing the racemic amines I is carried out in the presence of the amine of the formula $R^3NH_2$. When racemic amines in which $R^3$ is H are being prepared, the amine $R^3NH_2$ is ammonia.

Generally, the molar ratio of $R^3NH_2$ to the sum of optically active amine I and alcohol II and/or ketone III is from 1:1 to 50:1, preferably from 1.5:1 to 30:1, particularly preferably from 2:1 to 20:1, very particularly preferably from 2:1 to 10:1. The molar $R^3NH_2$ excess, based on the sum of optically active amine I and alcohol II and/or ketone III can in addition be greater than 50:1.

The molar ratio of optically active amine I to alcohol II and/or ketone III is not critical and can vary in broad ranges and is generally from 1:100 to 100:1, preferably from 1:50 to 50:1, for example 1:1.

The hydrogen is generally introduced into the reaction in an amount of from 5 to 400 l, preferably in an amount of from 10 to 200 l, per molar sum of optically active amine I and alcohol II and/or ketone III, with the liter values in each case being at STP.

When the process according to the invention is carried out in the gas phase, a mixture consisting of the optically active amine I and the corresponding secondary alcohol II and/or unsymmetrical ketone III is passed in a reactor, eg. an externally heated tubular reactor, in the gaseous state over the catalyst in a gas stream chosen to be sufficiently large for the evaporation comprising hydrogen and the amine $R^3NH_2$, preferably consisting of hydrogen and the amine $R^3NH_2$, at pressures of from 0.1 to 10 MPa, preferably from 0.1 to 5 MPa, particularly preferably from 0.1 to 3 MPa.

It is possible for the feed stream to flow into the fixed bed of catalyst from above or from below. The gas stream required is preferably obtained by means of a circulating gas procedure using, for example, a circulated gas flow of from about 5 to 10 m³/h (volume at STP) and a gas outflow of from about 250 to 350 l/h at a catalyst bed volume of 1 l. A typical circulation gas composition is, for example, about 40 to 45% by volume of $R_3NH_2$, remainder: $H_2$. The space velocity over the catalyst is generally in the range from 0.1 to 2 kg, preferably from 0.1 to 1 kg, particularly preferably from 0.3 to 0.8 kg, of starting material mixture [amine+(alcohol and/or ketone)] per liter of catalyst (bed volume) and hour.

The temperatures selected for the gas-phase racemization are in the range from 100 to 300° C., preferably from 150 to 270° C., particularly preferably from 160 to 250° C., very particularly preferably from 170 to 240° C., in particular from 180 to 230° C.

When the process according to the invention is carried out in the liquid phase, a mixture consisting of the optically active amine I and the corresponding secondary alcohol II and/or unsymmetrical ketone III is passed in the presence of hydrogen and the amine $R^3NH_2$ at pressures of from 0.1 to 30 MPa, preferably from 5 to 25 MPa, particularly preferably from 10 to 25 MPa, in the liquid state over the catalyst which is usually situated in a preferably externally heated fixed-bed reactor, eg. tubular reactor.

When the procedure is carried out in a tubular reactor it is possible for the direction of flow through the fixed catalyst bed to be either from the top (eg. trickle mode) or from the bottom (bottom mode). A circulation gas mode of operation is advantageous, in which case, for example, at a catalyst bed volume of 1 l, a circulation gas rate of approximately from 0.01 to 1 m³/h (volume converted to standard temperature and pressure) and an exhaust gas rate of from approximately 10 to 300 l/h are run.

The catalyst space velocity is generally in the range from 0.05 to 2, preferably from 0.1 to 1, particularly preferably from 0.2 to 0.6, kg of starting material mixture [amine+(alcohol and/or ketone)] per liter of catalyst (bed volume) and hour.

The temperatures chosen for the racemization in the liquid phase are from 100 to 300° C., preferably from 150 to 270° C., particularly preferably from 160 to 250° C., very particularly preferably from 170 to 240° C., in particular from 180 to 230° C.

The optically active amine I can be racemized in the liquid phase in the presence of an inert solvent which is liquid under the chosen reaction conditions, such as tetrahydrofuran, dioxane, N-methylpyrrolidone and/or ethylene glycol dimethyl ether.

Both when the process is carried out in the gas phase and in the liquid phase, the use of higher temperatures, higher overall pressures and higher catalyst space velocities as stated above is also possible.

The pressure in the reaction vessel which is essentially given by the sum of the partial pressures of optically active amine I, alcohol II and/or ketone III, the amine $R^3NH_2$, the racemized amine I formed, and the sol vent which m ay be present, at the temperature respectively employed, is expediently increased by compressing hydrogen to the desired reaction pressure.

After the reaction discharge has expediently been expanded, from it are removed (eg. by distillation) the hydrogen, the amine $R^3NH_2$ and any solvent used, with these being able to be recirculated, and the resultant cooled crude reaction product, which essentially comprises racemic amine I and water, is purified by a fractional rectification at atmospheric pressure or at reduced pressure. Preferably, before the fractional rectification is carried out, the majority of the water in the crude product is removed by treating with approximately 50% strength aqueous sodium hydroxide solution.

For example, according to the process of the invention, racemic 1-methoxy-2-aminopropane (R,S)-MOIPA) ($R^1$=—$CH_3$, $R^2$=—$CH_2OCH_3$, $R^3$=H) can be prepared by simultaneous in situ reaction of optically active 1-methoxy-2-aminopropane, 1-methoxy-2-propanol and ammonia in the presence of hydrogen and a hydrogenation catalyst or dehydrogenation catalyst at elevated temperature.

The crude process product which essentially comprises (R,S)-MOIPA and water can be worked up, for example, by adding sodium hydroxide solution to the discharge, separating off the aqueous phase and distilling the (R,S)-MOIPA-containing phase, in accordance with EP-A-881 211.

The advantage of the process of the invention is, inter alia, its particular economic efficiency, since no separate plants need to be built to prepare the racemic amines I by (a) amination of secondary alcohols II or unsymmetrical ketones III with amines of the formula $R^3NH_2$ and (b) racemizing the corresponding optically active amine I, but the processes (a) and (b) can be carried out simultaneously in situ (also compare in this context, the details on page 1 of the description, 2nd paragraph).

Surprisingly, the yields and selectivities of the individual process steps are virtually unaffected by the combination according to the invention of the two completely different abovementioned process steps (a) and (b) into a single process stage. That is to say, the increased formation of byproducts, for example the symmetrical amines of the formula

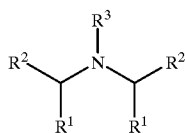

is virtually not seen.

Particularly suitable hydrogenation catalysts and dehydrogenation catalysts are catalysts which comprise, as catalytically active constituents, elements selected from the group consisting of copper, silver, gold, iron, cobalt, nickel, rhenium, ruthenium, rhodium, palladium, osmium, iridium, platinum, chromium, molybdenum and tungsten, in each case in metallic form (oxidation state 0) or in the form of compounds, eg. oxides, which are reduced to the corresponding metal under the process conditions.

The catalytically active constituents copper, silver, gold, iron, cobalt, nickel, rhenium, ruthenium, rhodium, palladium, osmium, iridium, platinum, chromium, molybdenum and/or tungsten are generally present in the catalytically active mass of the catalyst in amounts of from 0.1 to 80% by weight, preferably from 0.1 to 70% by weight, particularly preferably from 0.1 to 60% by weight, calculated as metal in oxidation state 0.

Preference is given to catalysts which comprise, as catalytically active constituents, elements selected from the group consisting of copper, silver, cobalt, nickel, ruthenium, rhodium, palladium, platinum, chromium and molybdenum, in particular selected from the group consisting of copper, silver, nickel, ruthenium, rhodium, palladium, chromium and molybdenum, in each case in metallic form (oxidation state 0) or in the form of compounds, eg. oxides, which are reduced to the corresponding metal under the process conditions.

Greater preference is given to catalysts which comprise the catalytically active constituents copper, silver, iron, cobalt, nickel, ruthenium, rhodium, palladium, osmium, iridium and/or platinum and a support material selected from the group consisting of aluminum oxide, zirconium dioxide, titanium dioxide, carbon and/or oxygen compounds of silicon.

The catalytically active mass of these catalysts which are preferably used in the process of the invention comprises the catalytically active constituents copper, silver, iron, cobalt, nickel, ruthenium, rhodium, palladium, osmium, iridium and/or platinum in total in amounts generally from 0.1 to 80% by weight, preferably from 0.1 to 70% by weight, particularly preferably from 0.1 to 60% by weight, calculated as metal in the oxidation state 0.

In addition, the catalytically active mass of these catalysts which are preferably used comprises the support materials aluminum oxide ($Al_2O_3$), zirconium dioxide ($ZrO_2$), titanium dioxide ($TiO_2$), carbon and/or oxygen compounds of silicon, calculated as $SiO_2$, generally in total in amounts of from 20 to 99.9% by weight, preferably from 30 to 99.9% by weight.

Examples of such catalysts are those disclosed in EP-A-839 575 comprising, based on the total weight of the catalyst, more than 6 and up to 50% by weight, of cobalt, nickel or their mixture, from 0.001 to 25% by weight of ruthenium, from 0 to 10% by weight of copper and from 0 to 5% by weight of promoters on a porous metal oxide support, such as aluminum oxide, aluminosilicate, titanium dioxide, zirconium dioxide or mixtures thereof, which can be prepared by (a) impregnating the support with the metals, promoters or compounds thereof, (b) drying and calcining the impregnated support and (c) reducing the calcined support in a hydrogen stream, and the catalysts disclosed in EP-A-839 574 comprising, based on the total weight of the catalyst, from 0.1 to 6% by weight of cobalt, nickel or their mixture, from 0.001 to 25% by weight of ruthenium, from 0 to 10% by weight of copper and from 0 to 5% by weight of promoters on a porous metal oxide support such as aluminum oxide, aluminosilicate, titanium dioxide, zirconium dioxide or mixtures thereof, which can be prepared by (a) impregnating the support with the metals, promoters or compounds thereof, (b) drying and calcining the impregnated support and (c) reducing the calcined support in a hydrogen stream.

Suitable catalysts for the process of the present invention are thin-layer catalysts in which the catalytically active components are applied to structured supports or monoliths, as are defined, for example, in the German application No. 198 27 385.1 of Jun. 27, 1998, page 1, lines 14 to 30, and in DE-A-35 13 726. The catalytically active components are applied to the structured support or monolith used, e.g. a metal wire mesh or an $SiO_2$—, $TiO_2$—, $ZrO_2$— or $Al_2O_3$ honeycomb body, by known methods, for example by vapor deposition of the catalytically active metal, e.g. noble metal, under reduced pressure as described in DE-A-35 13 726 or by an impregnation process as described in DE-A-41 35 055, DE-A-39 15 685 or U.S. Pat. No. 4,746,537.

Examples of thin-layer catalysts which can be used in the process of the present invention are the catalysts disclosed in EP-A-646 562 in Examples 1 and 2 which comprise the material No. 1.4767 (Kanthal) and vapor-deposited Pd, the catalyst disclosed in Example 3 which comprises the material No. 1.4401 and vapor-deposited Pd and the catalyst disclosed in Example 4 which comprises the material No. 1.4301 and vapor-deposited Pd. (Material numbers as given in "Stahleisenliste", Verlag Stahleisen mbH 1990, 8th edition, p. 87ff).

Further hydrogenation and dehydrogenation catalysts which are suitable for use in the process of the present invention are shell catalysts in which the catalytically active composition has been applied in the form of a shell on a core of support material which is generally inert under the reaction conditions, for example quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures thereof.

Such shell catalysts are usually prepared using impregnation processes as are described in J.-F. Le Page et al., Applied Heterogeneous Catalysis, Edition Technip Paris, 1987, ISBN 2-7108-0531-6, pages 106 to 123. These impregnation processes comprise (a) impregnation of the support material with an excess of solution (immersion) or (b) spray impregnation of the support material in an impregnation drum, followed in each case by drying and calcination.

Another possible way of preparing such shell catalysts is described, for example, in DE-A-16 42 938 and DE-A-17 69 998. In this method, an aqueous and/or organic solvent-containing solution or suspension of the constituents of the catalytically active composition and/or their precursor compounds, hereinafter referred to as the "slurry", is sprayed onto the support material in a heated coating drum at elevated temperature until the desired proportion by weight of catalytically active composition in the overall catalyst has been reached. According to DE-A-21 06 796, coating can also be carried out in fluidized-bed coaters, as are described, for example, in DE-A-12 80 756. The slurry can, if desired, include organic binders, preferably copolymers such as vinyl acetate-vinyl laurate or vinyl acetate-ethylene, as taught by EP-A-744 214.

Examples of shell catalysts which can be used in the process of the present invention are the catalysts disclosed in DE-A-20 59 978, Example 1 (cat. A), which are prepared by impregnation of alumina agglomerates with an aqueous noble metal salt solution, e.g. Pd salt solution, and subsequent drying and calcination, and the catalysts disclosed in the abovementioned article by J.-F. Le Page et al. (Applied Heterogeneous Catalysis), e.g. on page 110, which are prepared by impregnation and comprise $Al_2O_3$ and Ni and/or Co.

In general, the catalysts in the process of the present invention can also be used in the form of catalysts which have been obtained by impregnation, precipitation or peptization processes and which consist entirely of catalytically active composition and, if desired, a shaping aid (e.g. graphite or stearic acid) if the catalyst is used as a shaped body, i.e. no further catalytically inactive accompanying materials.

As supports, preference is given to using oxidic, carbidic or nitridic materials, particularly preferably materials of an oxidic nature.

In this context, materials used as catalyst supports, for example titanium dioxide ($TiO_2$; anatase, rutile), aluminum oxide ($Al_2O_3$; preferably $\alpha$-, $\beta$-, $\gamma$- or $\theta$-$Al_2O_3$; D10-10 from BASF; $Al_2O_3$ having a large surface area prepared by bringing at least one precursor of aluminum oxide into contact with at least one structure former in a liquid medium, e.g. as described in the German application No. 197 30 126.6 of Jul. 14, 1997), zirconium dioxide ($ZrO_2$; preferably in the monoclinic or tetragonal form), silicon dioxide ($SiO_2$; e.g. $SiO_2$ obtained by precipitation from water glass or by the sol-gel method or mesoporous $SiO_2$, e.g. mesoporous $SiO_2$ having a specific surface area of the mesopores of at least 500 $m^2/g$ and a pore volume of the mesopores of at least 1.0 ml/g as described in DE-A-196 39 016, or silica gel e.g. as described in Ullmann, Enzykl. Techn. Chem., 4th edition, Volume 21, pp. 457–63, 1982) or in the form of silicates such as kaolin, hectorite or aluminosilicates (e.g. as described in Nature, Volume 359, pp. 710–12, 1992, or alkali metal or alkaline earth metal aluminosilicates (zeolites), e.g. of the formula $M_{2/z}O.Al_2O_3.xSiO_2.yH_2O$, where M is a monovalent or polyvalent metal, H, [$NH_4$], z is the valence, x=1.8 to about 12 and y=0 to about 8), magnesium silicates (e.g. steatite), zirconium silicates, cerium silicates or calcium silicates) or $SiO_2$ having a large surface area prepared by bringing at least one precursor of silicon dioxide into contact with at least one structure former in a liquid medium, e.g. as described in the German application No. 197 32 865.2 of Jul. 30, 1997), clays which consist predominantly of phyllosilicates and/or chain silicates (e.g. bentonite or montmorillonite), pumice, silicon carbide, magnesium oxide (MgO), zinc oxide (ZnO), tin dioxide ($SnO_2$), cerium dioxide ($CeO_2$), and/or carbon (e.g. activated carbon or graphite in extruded or pelletized form), and mixtures thereof, are counted as being part of the catalytically active composition.

The catalysts are used, for example, by introducing the catalytically active composition ground to powder form into the reactor or preferably placing the catalytically active composition, after milling, mixing with shaping aids, shaping and heat treatment, as shaped catalyst bodies, for example as pellets, spheres, rings or extrudates, in the reactor.

Various methods of preparing these catalysts are possible.

They are obtainable, for example, by peptization of pulverulent mixtures of the hydroxides, carbonates, oxides and/or other salts of the catalyst components with water and subsequent extrudation and heat treatment of the composition obtained in this way.

The catalysts used in the process of the present invention can also be prepared by impregnation of the catalyst support materials (see above) or mixtures of two or more of these catalyst support materials which are, for example, in the form of powder or shaped bodies such as extrudates, pellets, spheres or rings.

The shaped bodies of the abovementioned catalyst support materials can be produced by the customary methods.

The impregnation of the catalyst support material is likewise carried out by the customary methods, as described, for example, in EP-A-599 180, EP-A-673 918 or A. B. Stiles, Catalyst Manufacture -Laboratory and Commercial Preparations, Marcel Dekker, New York (1983), by application of an appropriate metal salt solution in one or more impregnation steps, using, for example, appropriate nitrates, acetates or chlorides as metal salts. After the impregnation, the composition is dried and, if desired, calcined.

The impregnation can be carried out by the incipient wetness method in which the catalyst support material is, depending on its water absorption capacity, moistened to at most saturation with the impregnation solution. However, the impregnation can also be carried out in supernatant solution.

In multistage impregnation processes, it is advantageous to dry and possibly calcine the support material between individual impregnation steps. It is particularly advantageous to employ multistage impregnation when the catalyst support material is to be loaded with a relatively large amount of metal.

To apply a plurality of metal components to the catalyst support material, the impregnation can be carried out simultaneously with all metal salts or successively in any order of the individual metal salts.

It is also possible to employ precipitation methods to prepare the catalysts used in the process of the present invention. Thus, for example, they can be obtained by coprecipitation of the metal components from an aqueous salt solution containing these elements by means of mineral bases in the presence of a slurry or suspension of fine powders of the sparingly soluble catalyst support material and subsequent washing, drying and calcination of the precipitate obtained. Sparingly soluble catalyst support materials which can be used are, for example, aluminum oxide, titanium dioxide, silicon dioxide, zirconium dioxide and/or hydrated zirconium oxide.

The catalysts used in the process of the present invention can be prepared by coprecipitation of all their components. For this purpose, an aqueous salt solution containing the catalyst components is conveniently admixed hot and while stirring with an aqueous mineral base, in particular an alkali metal base, for example sodium carbonate, sodium hydroxide, potassium carbonate or potassium hydroxide, until precipitation is complete. The type of salts used is generally not critical: since the water-solubility of the salts is of prime importance in this procedure, a criterion is that they have the good water-solubility necessary to prepare these comparatively highly concentrated salt solutions. It is considered self evident that, when selecting the salts of the individual components, only salts containing anions which do not lead to problems, whether by causing undesirable precipitation or by hindering or preventing precipitation by complex formation, will be selected.

The precipitates obtained in these precipitation reactions are generally chemically nonuniform and comprise, inter alia, mixtures of the oxides, hydrated oxides, hydroxides, carbonates and insoluble and basic salts of the metals used. To improve the filterability of the precipitates, it may prove to be useful to age them, i.e. to leave them to stand for some time after the precipitation, possibly at elevated temperature or while passing air through the suspension.

The precipitates obtained by these precipitation methods are further processed by customary methods to give the catalyst. After washing, they are generally dried at from 80 to 200° C., preferably from 100 to 150° C., and then calcined. The calcination is generally carried out at from 300 to 800° C., preferably from 400 to 600° C., in particular from 450 to 550° C.

After calcination, the catalyst is advantageously conditioned, whether by adjusting it to a particular particle size by milling or by mixing it after milling with shaping aids such as graphite or stearic acid, pressing it into compacts, e.g. pellets, by means of a press and heat treating it. The heat treatment temperatures generally correspond to the calcination temperatures.

In the catalysts prepared in this way, the catalytically active metals are present in the form of a mixture of their oxygen-containing compounds, i.e. particularly as oxides and mixed oxides.

The catalysts prepared in this way are usually prereduced before they are used for the racemization of the optically active amines I. However, they can also be used without prereduction, in which case they are then reduced under the conditions of the racemization by the hydrogen present in the reactor.

For the prereduction, the catalysts are generally first exposed to a nitrogen/hydrogen atmosphere at from 150 to 200° C. for a period of from 12 to 20 hours and subsequently treated in a hydrogen atmosphere at from 200 to 400° C. for up to about 24 hours. In this prereduction, part of the oxygen-containing metal compounds present in the catalysts are reduced to the corresponding metals, so that these together with the various oxygen compounds are present in the active form of the catalyst.

The following concentration figures (in % by weight) of the components of the catalyst are in each case based, unless otherwise indicated, on the mass of the catalytically active composition of the finished catalyst after its last heat treatment and before its reduction with hydrogen.

The mass of the catalytically active composition of the catalyst after its last heat treatment and before its reduction with hydrogen is defined as the sum of the masses of the catalytically active constituents, where in the case of the abovementioned catalysts prepared by peptization, impregnation or precipitation, materials used as catalyst supports are included as part of the catalytically active composition.

The sum of the abovementioned constituents of the catalytically active composition is usually from 70 to 100% by weight, particularly from 80 to 100% by weight, in particular from 90 to 100% by weight, very particularly from 95 to 100% by weight, for example 100% by weight.

The catalytically active composition of the catalysts used in the process of the present invention can further comprise one or more elements (oxidation state 0) or their inorganic or organic compounds selected from groups I A to VI A and I B to VII B of the Periodic Table.

Examples of such elements and their compounds are:

transition metals and compounds thereof such as Mn, $Mn_2O_3$ and $MnO_2$; V, vanadium oxides and vanadyl pyrophosphate; Nb, niobium oxides and niobium oxalate; Ta and tantalum oxides; lanthanides such as Ce and $CeO_2$, Pr and $Pr_2O_3$; alkali metal oxides such as $Na_2O$; alkali metal carbonates; alkaline earth metal oxides such as MgO, CaO, SrO and BaO; alkaline earth metal carbonates such as $MgCO_3$, $CaCO_3$ and $BaCO_3$; boron oxide ($B_2O_3$).

In the process of the present invention, preference is given to using catalysts whose catalytically active composition after the final heat treatment and before reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or carbon (e.g. as activated carbon or graphite) and/or oxygen-containing compounds of silicon, calculated as $SiO_2$, from 1 to 70% by weight, preferably from 2 to 65% by weight, particularly preferably from 4 to 60% by weight, very particularly preferably from 20 to 60% by weight, of oxygen-containing compounds of copper, calculated as CuO, from 0 to 70% by weight, preferably from 1 to 70% by weight, particularly preferably from 5 to 66% by weight, of oxygen-containing compounds of nickel, calculated as NiO, and from 0 to 50% by weight, preferably from 0 to 30% by weight, for example from 0.1 to 25% by weight, of oxygen-containing compounds of cobalt, calculated as CoO, oxygen-containing compounds of chromium, calculated as $Cr_2O_3$, oxygen-containing compounds of zinc, calculated as ZnO, oxygen-containing compounds of molybdenum, calculated as $MoO_3$, oxygen-containing compounds of manganese, calculated as $MnO_2$, oxygen-containing compounds of magnesium, calculated as MgO, oxygen-containing compounds of calcium, calculated as CaO, and/or oxygen-containing compounds of barium, calculated as BaO.

Examples of such catalysts are the catalysts disclosed in DE-A-19 53 263 comprising cobalt, nickel and copper and aluminum oxide and/or silicon dioxide and having a metal content of from 5 to 80% by weight, based on the total catalyst, where the catalysts comprise, calculated on the basis of the metal content, from 70 to 95% by weight of a mixture of cobalt and nickel and from 5 to 30% by weight of copper and the weight ratio of cobalt to nickel is from 4:1 to 1:4, for example the catalysts described in loc. cit. in the examples, which comprise from 2 to 4% by weight of copper oxide, 10% by weight of cobalt oxide and 10% by weight of nickel oxide on aluminum oxide, the catalysts disclosed in EP-A-382 049, whose catalytically active composition before reduction with hydrogen comprises from 20 to 85% by weight of $ZrO_2$, from 1 to 30% by weight of CuO and from 1 to 40% by weight of each of CuO and NiO, for example the catalysts described in loc. cit. on page 6 which have the composition 76% by weight of Zr, calculated as $ZrO_2$, 4% by weight of Cu, calculated as CuO, 10% by weight of Co, calculated as CoO, and 10% by weight of Ni, calculated as NiO, the catalysts disclosed in EP-A-696 572, whose catalytically active composition before reduction with hydrogen comprises from 20 to 85% by weight of $ZrO_2$, from 1 to 30% by weight of oxygen-containing compounds of copper, calculated as CuO, from 30 to 70% by weight of oxygen-containing compounds of nickel, calculated as NiO, from 0.1 to 5% by weight of oxygen-containing compounds of molybdenum, calculated as $MoO_3$, and from 0 to 10% by weight of oxygen-containing compounds of aluminum and/or manganese, calculated as $Al_2O_3$ and $MnO_2$ respectively, for example the catalyst disclosed in loc. cit., page 8, which has the composition 31.5% by weight of $ZrO_2$, 50% by weight of NiO, 17% by weight of CuO and 1.5% by weight of $MoO_3$, the catalysts disclosed in the German application No. 19826396.1 of Jun. 12, 1998, whose catalytically active composition before reduction with hydrogen comprises from 22 to 40% by weight of $ZrO_2$, from 1 to 30% by weight of oxygen-containing compounds of copper, calculated as CuO, from 15 to 50% by weight of oxygen-containing compounds of nickel, calculated as NiO, with the molar Ni:Cu ratio being greater than 1, from 15 to 50% by weight of oxygen-containing compounds of cobalt, calculated as CoO, from 0 to 10% by weight of oxygen-containing compounds of aluminum and/or manganese, calculated as $Al_2O_3$ and $MnO_2$ respectively, and no oxygen-containing compounds of molybdenum, for example the catalyst (A) disclosed in loc. cit., page 17, which has the composition 33% by weight of Zr, calculated as $ZrO_2$, 28% by weight of Ni, calculated as NiO, 11% by weight of Cu, calculated as CuO, and 28% by weight of Co, calculated as CoO, the catalysts disclosed in the German application No. 19742911.4 of Sep. 29, 1997, whose catalytically active composition before reduction with hydrogen comprises from 20 to 85% by weight of $ZrO_2$, from 1 to 30% by weight of oxygen-containing compounds of copper, calculated as CuO, from 14 to 70% by weight of oxygen-containing compounds of nickel, calculated as NiO, with the Ni:Cu ratio being greater than 1, from 0 to 10% by weight of oxygen-containing compounds of aluminum and/or manganese, calculated as $Al_2O_3$ and $MnO_2$ respectively, and no oxygen-containing compounds of cobalt or molybdenum, for example the catalyst (A) disclosed in loc. cit., page 14 to 15, which has the composition 32% by weight of Zr, calculated as $ZrO_2$, 51% by weight of Ni, calculated as NiO, and 17% by weight of Cu, calculated as CuO, the catalysts which are disclosed in EP-A-284 919 and have the formula $M_xMg_y(SiO_2) \cdot nH_2O$, where M is a divalent, reducible metal atom selected from the group consisting of Cu, Fe, Co and Ni, x and y are numbers which together can reach the value 1.5 and n is, expressed in % by weight after drying, from 0 to 80, for example the catalyst described in loc. cit. in the example which comprises 35% of CuO, 9% of MgO and 38% of $SiO_2$ and the catalyst described in EP-A-863 140 on page 3 which comprises from 45 to 47% by weight of CuO, magnesium silicate comprising from about 15 to 17% by weight of MgO and from 35 to 36% by weight of $SiO_2$, about 0.9% by weight of $Cr_2O_3$, about 1% by weight of BaO and about 0.6% by weight of ZnO, the catalysts which are disclosed in DE-A-24 45 303 and are obtainable by heat-treating a basic copper- and aluminum-containing carbonate of the composition $Cu_mAl_6$ $(CO_3)_{0.5m}O_3(OH)_{m+12}$, where m is any, even nonintegral, number from 2 to 6, at from 350 to 700° C., for example the copper-containing precipitated catalyst disclosed in loc. cit., Example 1, which is prepared by treating a solution of copper nitrate and aluminum nitrate with sodium bicarbonate and subsequently washing, drying and heat-treating the precipitate, the supported catalysts disclosed in WO 95/32171 and EP-A-816 350 comprising from 5 to 50% by weight, preferably from 15 to 40% by weight, of copper, calculated as CuO, from 50 to 95% by weight, preferably from 60 to 85% by weight, of silicon, calculated as $SiO_2$, from 0 to 20% by weight of magnesium, calculated as MgO, from 0 to 5% by weight of barium, calculated as BaO, from 0 to 5% by weight of zinc, calculated as ZnO, and from 0 to 5% by weight of chromium, calculated as $Cr_2O_3$, in each case based on the total weight of the calcined catalyst, for example the catalyst disclosed in EP-A-816 350, page 5, which comprises 30% by weight of CuO and 70% by weight of $SiO_2$, the catalysts disclosed in EP-A-514 692, whose catalytically active composition before reduction with hydrogen comprises from 5 to 100% by weight of an oxide of copper and nickel in an atom ratio of from 1:1 to 10:1 and zirconium oxide and/or aluminum oxide, in particular the catalysts disclosed in loc. cit. on page 3, lines 20 to 30, whose catalytically active composition before reduction with hydrogen comprises from 20 to 80% by weight, particularly from 40 to 70% by weight, of $Al_2O_3$ and/or $ZrO_2$, from 1 to 30% by weight of CuO, from 1 to 30% by weight of NiO and possibly from 1 to 30% by weight of CoO, for example the catalyst described in loc. cit., Example 1, which comprises (after activation) 55% by weight of $Al_2O_3$, 36% by weight of Cu and 7% by weight of Ni, the catalysts disclosed in EP-A-691 157 comprising (before reduction with $H_2$) from 85 to 100% by weight, in particular from 95 to 100% by weight, of copper oxide and zirconium dioxide and from 0 to 15% by weight, in particular from 0 to 5% by weight, of metal oxides of transition groups Ib to VIIb and VIII of the Periodic Table, for example the catalyst described in loc. cit., pages 5 to 6, which has the composition 52.6% by weight of CuO and 47.4% by weight of $ZrO_2$, and the catalysts disclosed in the German Application No. 19859776.2 of Dec. 23, 1998 comprising copper and oxygen-containing compounds of titanium, where the catalyst is used in the form of shaped bodies which have been produced with addition of metallic copper powder, for example catalysts whose catalytically active composition before reduction with hydrogen comprises from 20 to 83% by weight of oxygen-containing compounds of titanium, calculated as $TiO_2$, from 15 to 60% by weight of oxygen-containing compounds of copper, calculated as CuO, and from 2 to 29% by weight of metallic copper which has been added before shaping the catalyst material.

In the process of the present invention, preference is given to using catalysts whose catalytically active composition contains less than 20% by weight, preferably less than 10% by weight, in particular less than 5% by weight and very particularly less than 1% by weight, of cobalt, calculated as CoO. Very particularly preferably, the catalytically active composition contains no catalytically active amounts of cobalt or its compounds.

In the process of the present invention, particular preference is given to using catalysts whose catalytically active composition after the final heat treatment before reduction with hydrogen comprises from 20 to 85% by weight, preferably from 25 to 80% by weight, particularly preferably from 30 to 75% by weight, of aluminum oxide ($Al_2O_3$) and/or zirconium dioxide ($ZrO_2$) and/or titanium dioxide ($TiO_2$) and/or oxygen-containing compounds of silicon, calculated as $SiO_2$.

In particular, use is made of catalysts whose catalytically active composition after the final heat treatment and before reduction with hydrogen comprises from 35 to 75% by weight of aluminum oxide ($Al_2O_3$), from 20 to 60% by weight of oxygen-containing compounds of copper, calculated as CuO, and from 5 to 45% by weight, preferably from 5 to 20% by weight, of oxygen-containing compounds of nickel, calculated as NiO, where the sum of these components is at least 80% by weight, preferably at least 90% by weight, particularly preferably at least 95% by weight, for example 100% by weight.

Such catalysts can be prepared, for example, as described in EP-A-514 692, page 3, lines 24 to 30. For example, loc. cit., Example 1, describes a catalyst comprising (after activation) 55% by weight of $Al_2O_3$, 36% by weight of Cu and 7% by weight of Ni.

The radicals $R^1$, $R^2$ and $R^3$, where $R^1$ and $R^2$ are different are, independently of one another, alkyl, cycloalkyl, arylalkyl, aryl, heteroaryl and heterocyclic radicals and $R^3$ can also be H, where the radicals may be substituted by substituents which are inert under the reaction conditions and are selected from the group consisting of alkyl, cycloalkyl, alkoxy, aryloxy, amino, alkylamino and dialkylamino.

$R^1$, $R^2$ and $R^3$ are preferably:

linear or branched alkyl radicals such as $C_1$–$C_{20}$-alkyl, particularly preferably $C_1$–$C_{12}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl, isododecyl, very particularly preferably $C_1$–$C_8$-alkyl, such as methyl, ethyl, n-propyl, isopropyl, n-butyl, isobutyl, sec-butyl, tert-butyl and 2-ethylhexyl, cycloalkyl radicals, preferably $C_3$–$C_8$-cycloalkyl, such as cyclopropyl, cyclobutyl, cyclopentyl, cyclohexyl, cycloheptyl and cyclooctyl, particularly preferably cyclopentyl, cyclohexyl and cyclooctyl, very particularly preferably cyclopentyl and cyclohexyl, arylalkyl radicals, preferably $C_7$–$C_{20}$-arylalkyl, such as benzyl, 1-phenethyl, 2-phenethyl, 1-naphthylmethyl, 2-naphthylmethyl, phenanthrylmethyls, 4-tert-butylphenylmethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, aromatic radicals, preferably $C_6$–$C_{20}$-aryl, such as phenyl, 1-naphthyl, 2-naphthyl, 1-anthryl, 2-anthryl, 9-anthryl, particularly preferably phenyl, 1-naphthyl and 2-naphthyl, particularly preferably phenyl, heteroaromatic radicals, preferably $C_3$–$C_{15}$-heteroaryl, such as 2-pyridyl, 3-pyridyl, 4-pyridyl, quinolyl, pyrazyl, pyrrol-3-yl, thienyl, imidazol-2-yl, 2-furanyl and 3-furanyl, and heterocyclic radicals, preferably $C_3$–$C_{15}$-heterocycloalkyl, such as N-alkylpiperidin-3-yl, N-alkylpiperidin-4-yl, N,N'-dialkylpiperazin-2-yl, tetrahydrofuran-3-yl and N-alkylpyrrolidin-3-yl, where in these cases the radicals R can, independently of one another, bear substituents which are inert under the reaction conditions, e.g. $C_1$–$C_{20}$-alkyl, $C_3$–$C_8$-cycloalkyl, $C_1$–$C_{20}$-alkoxy, $C_6$–$C_{20}$-aryloxy, amino, $C_1$–$C_{20}$-alkylamino and $C_2$–$C_{20}$-dialkylamino.

The number of these substituents on R can be, depending on the type of radical, from 0 to 5, preferably from 0 to 3, in particular 0, 1 or 2. Possible substituents are, in particular:

$C_1$–$C_{20}$-alkyl, as defined above, $C_3$–$C_8$-cycloalkyl, as defined above, $C_1$–$C_{20}$-alkoxy, preferably $C_1$–$C_8$-alkoxy, such as methoxy, ethoxy, n-propoxy, isopropoxy, n-butoxy, isobutoxy, sec-butoxy, tert-butoxy, n-pentoxy, isopentoxy, sec-pentoxy, neo-pentoxy, 1,2-dimethylpropoxy, n-hexoxy, isohexoxy, sec-hexoxy, n-heptoxy, isoheptoxy, n-octoxy, isooctoxy, particularly preferably $C_1$–$C_4$-alkoxy, such as methoxy, ethoxy, n-propoxy, isopropoxy, n-butoxy, isobutoxy, sec-butoxy and tert-butoxy, $C_6$–$C_{20}$-aryloxy, such as phenoxy, 1-naphthoxy and 2-naphthoxy, preferably phenoxy, amino (—$NH_2$), $C_1$–$C_{20}$-alkylamino, preferably $C_1$–$C_{12}$-alkylamino, particularly $C_1$–$C_8$-alkylamino, such as methylamino, ethylamino, n-propylamino, isopropylamino, n-butylamino, isobutylamino, tert-butylamino, cyclopentylamino and cyclohexylamino, and $C_2$–$C_{20}$-dialkylamino, preferably $C_2$–$C_{12}$-dialkylamino, particularly $C_2$–$C_8$-dialkylamino, for example N,N-dimethylamino, N,N-diethylamino, N,N-di-n-propylamino, N,N-di-isopropylamino, N,N-di-n-butylamino, N-ethyl-N-methylamino, N-methyl-N-propylamino and dicyclohexylamino.

$R^3$ is very particularly preferably hydrogen (H).

Examples of amines I which can be used in the process of the present invention are:

1-methoxy-2-aminopropane (MOIPA), 2-amino-3-methylbutane, 2-amino-3,3-dimethylbutane, 1-phenylethylamine, 1-naphthylethylamine, 2-naphthylethylamine, 1-phenylpropylamine, 2-amino-1-phenylpropane, 2-amino-1-(p-hydroxyphenyl) propane, 2-amino-1-(p-trifluoromethylphenyl)propane, 2-amino-1-cyclohexylpropane, 2-amino-6-methylheptane, 2-aminoheptane, 2-amino-4-methylhexane, 1-(4-methylphenyl)ethylamine, 1-(4-methoxyphenyl)ethylamine, 1-(3-methoxyphenyl) ethylamine, 1-aminotetralin, trans-1-amino-2-benzyloxycyclopentane and trans-1-amino-2-benzyloxycyclohexane.

Particular preference is given to 1-methoxy-2-aminopropane, 2-amino-3-methylbutane and 2-amino-3,3-dimethylbutane.

In a particular variant, the process of the present invention is carried out using an optically active amine I which has been obtained by cleavage of an amide derived from this optically active amine, which amide is formed in the preparation of one enantiomer of I (based on the asymmetric carbon atom shown in I) by (a) enantioselective acylation of the racemic amine I with an ester whose acid component bears a fluorine, nitrogen, phosphorus, oxygen or sulfur atom adjacent to the carbonyl carbon in the presence of a hydrolase and (b) separation of the resulting mixture of optically active amine I and amide.

In a further particular variant, the process of the present invention is carried out using an optically active amine I which has been obtained in the preparation of one enantiomer of I (based on the asymmetric carbon atom shown in I) by (a) enantioselective acylation of the racemic amine I with an ester whose acid component bears a fluorine, nitrogen, phosphorus, oxygen or sulfur atom adjacent to the carbonyl carbon in the presence of a hydrolase, (b) separation of the resulting mixture of optically active amine I and amide and (c) isolation of the other enantiomer of I by cleavage of the amide.

The methods of preparing optically active amines I from the corresponding racemates by (a) enantioselective acylation of the racemic amine I with an ester whose oxygen component bears a fluorine, nitrogen, phosphorus, oxygen or sulfur atom adjacent to the carbonyl carbon in the presence of a hydrolase and (b) separation of the resulting mixture of optically active amine I and amide and (c) isolation of the other enantiomer of I by cleavage of the amide are described in WO 95/08636 and WO 96/23894.

The hydrolase is, for example, a lipase, in particular a microbial lipase. The ester is, for example, a $C_1$–$C_{12}$-alkyl ester of a $C_1$–$C_4$-alkoxy acetic acid, e.g. ethyl methoxyacetate.

The cleavage of the amide derived from the optically active amine I with retention of the configuration of the center of chirality can be carried out by hydrolysis, for example by hydrolysis in the presence of a polyol or an aminoalcohol and an alkali metal hydroxide or alkaline earth metal hydroxide as described in WO 97/10201.

These particular process variants are particularly economical since, after the preparation of the desired enantiomer of the amine I, e.g. as described in WO 95/08636 or WO 96/23894, the remaining, undesired enantiomer of I is racemized by the process of the present application and is returned to the process for preparing the desired enantiomer of I, e.g. as described in WO 95/08636 or WO 96/23894. In this way it is possible to obtain a total of more than 50% of the desired enantiomer from the racemic amine I. (cf. also the discussion on page 1 of the present description, 2nd paragraph).

EXAMPLES

Example 1

Preparation of racemic MOIPA by continuously reacting (R)-1-methoxyisopropylamine ((R)-MOIPA), 1-methoxyisopropanol and ammonia in the gas phase A 1:1 molar mixture of (R)-1-methoxyisopropylamine ((R)-MOIPA) and (racemic 1-methoxyisopropanol having a total water content of 5% by weight together with ammonia and hydrogen were fed via a preheater into a tube reactor operated at 15 bar gauge pressure. The reactor was at 190 to 210° C.; and the circulating gas flow was about 7 standard $m^3/(l_{cat.}*h)$. A small gas output of about 300 standard $l/(l_{cat.}*h)$ was taken off.

The reactor had been charged with a precipitated catalyst having the composition 45% by weight of CuO, 10% by weight of NiO and 45% by weight of γ-$Al_2O_3$ support. Before commencement of the reaction, the catalyst was reduced at 240° C. in a stream of hydrogen. The molar ratio of (R)-MOIPA to ammonia was 1:6 and the space velocity over the catalyst was 0.3 kg of (R)-MOIPA, 0.3 kg of 1-methoxyisopropanol and 0.29 kg of ammonia per liter of catalyst (bed volume) and per hour. The reactor output was depressurized in a separator and worked up by distillation.

GC analysis of the product (ammonia- and water-free) in % by GC area; the enantiomer distribution was determined by chiral HPLC analysis:

| | | |
|---|---|---|
| (R)- + (S)-MOIPA | 96.4 | [(R)-MOIPA:(S)-MOIPA = 50.2:49.8] |
| Methanol | 0.2 | |
| Isopropylamine | 0.3 | |
| Octylamine | 0.1 | |
| Others | 3.0 | |
| Degree of racemization: | 99.2% | |
| Racemate yield: | 96% | (based on (R)-MOIPA used and 1-methoxyisopropanol). |

Example 2

Preparation of racemic MOIPA by continuously reacting (R)-1-methoxyisopropylamine ((R)-MOIPA), 1-methoxyisopropanol and ammonia in the gas phase In a similar manner to Example 1, a 1:1 molar mixture of (R)-1-methoxyisopropylamine ((R)-MOIPA) and 1-methoxyisopropanol was used, but this had a total water content of 23% by weight.

GC analysis of the product (ammonia- and water-free) in % by GC area; the enantiomer distribution was determined by chiral HPLC analysis:

| | | |
|---|---|---|
| (R)- + (S)-MOIPA | 93.7 | [(R)-MOIPA:(S)-MOIPA = 50.4:49.61 |
| Methanol | 0.1 | |
| Isopropylamine | 0.5 | |
| Methoxyisopropanol | 1.7 | |
| Octylamine | 1.3 | |
| Others | 2.7 | |
| Degree of racemization: | 98.4% | |
| Racemate yield: | 93% | (based on (R)-MOIPA) used and 1-methoxyisopropanol). |

We claim:
1. A process for the preparation of racemic amines of the formula I

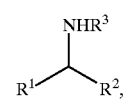

(I)

where $R^1$ and $R^2$ are different and $R^1$, $R^2$, $R^3$ are alkyl, cycloalkyl, arylalkyl, aryl, heteroaryl and heterocyclic radicals and $R^3$ can also be hydrogen, where the radicals can bear substituents selected from the group consisting of alkyl, cycloalkyl, alkoxy, aryloxy, amino, alkylamino and dialkylamino, which comprises simultaneously reacting in situ the corresponding optically active amine I and the secondary alcohol of the formula II and/or the unsymmetrical ketone of the formula III

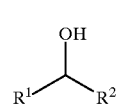

(II)

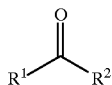
(III)

and the amine of the formula $R^3NH_2$ in the presence of hydrogen and a hydrogenation catalyst or dehydrogenation catalyst at elevated temperature.

2. A process as claimed in claim 1, wherein the reaction is carried out in the presence of a catalyst comprising the catalytically active constituents copper, silver, gold, iron, cobalt, nickel, rhenium, ruthenium, rhodium, palladium, osmium, iridium, platinum, chromium, molybdenum and/or tungsten.

3. A process as claimed in claim 1, wherein the reaction is carried out in the presence of a catalyst comprising the catalytically active constituents copper, silver, iron, cobalt, nickel, ruthenium, rhodium, palladium, osmium, iridium and/or platinum and a support material selected from the group consisting of aluminum oxide, zirconium dioxide, titanium dioxide, carbon and/or oxygen-containing compounds of silicon.

4. A process as claimed in claim 1, wherein the reaction is carried out in the presence of a catalyst whose catalytically active composition before reduction with hydrogen comprises from 20 to 85% by weight of aluminum oxide ($Al_2O_3$), zirconium dioxide ($ZrO_2$), titanium dioxide ($TiO_2$), carbon and/or oxygen-containing compounds of silicon, calculated as $SiO_2$, from 1 to 70% by weight of oxygen-containing compounds of copper, calculated as CuO, from 0 to 70% by weight of oxygen-containing compounds of nickel, calculated as NiO, and from 0 to 50% by weight of oxygen-containing compounds of cobalt, calculated as CoO, oxygen-containing compounds of chromium, calculated as $Cr_2O_3$, oxygen-containing compounds of zinc, calculated as ZnO, oxygen-containing compounds of molybdenum, calculated as $MoO_3$, oxygen-containing compounds of manganese, calculated as $MnO_2$, oxygen-containing compounds of magnesium, calculated as MgO, oxygen-containing compounds of calcium, calculated as CaO, and/or oxygen-containing compounds of barium, calculated as BaO.

5. A process as claimed in claim 1, wherein the reaction is carried out in the presence of a catalyst whose catalytically active composition before reduction with hydrogen comprises from 35 to 75% by weight of aluminum oxide ($Al_2O_3$), from 20 to 60% by weight of oxygen-containing compounds of copper, calculated as CuO, and from 5 to 45% by weight of oxygen-containing compounds of nickel, calculated as NiO, where the sum of these components is at least 80% by weight.

6. A process as claimed in claim 1, wherein the reaction is carried out in the presence of a catalyst which, based on the total weight of the catalyst, comprises from >6 to 50% by weight of cobalt, nickel or a mixture thereof, from 0.001 to 25% by weight of ruthenium, from 0 to 10% by weight of copper and from 0 to 5% by weight of promoters on a porous metal oxide support.

7. A process as claimed in claim 1, wherein the reaction is carried out in the presence of a catalyst which, based on the total weight of the catalyst, comprises from 0.1 to 6% by weight of cobalt, nickel or a mixture thereof, from 0.001 to 25% by weight of ruthenium, from 0 to 10% by weight of copper and from 0 to 5% by weight of promoters on a porous metal oxide support.

8. A process as claimed in claim 1, wherein the reaction is carried out at from 150 to 270° C.

9. A process as claimed in claim 1, wherein the reaction is carried out at a pressure of from 0.1 to 30 MPa.

10. A process as claimed in claim 1, wherein the optically active amine used is 1-methoxy-2-aminopropane, 2-amino-3-methyl-butane or 2-amino-3,3-dimethylbutane.

11. A process as claimed in claim 1, wherein the optically active amine I has been obtained by cleavage of an amide derived from this optically active amine, which amide is formed in the preparation of one enantiomer of I by (a) enantioselective acylation of the racemic amine I with an ester whose acid component bears a fluorine, nitrogen, phosphorus, oxygen or sulfur atom adjacent to the carbonyl carbon in the presence of a hydrolase and (b) separation of the resulting mixture of optically amine I and amide.

12. A process as claimed in claim 1, wherein the optically active amine I has been obtained in the preparation of one enantiomer of I by (a) enantioselective acylation of the racemic amine I with an ester whose acid component bears a fluorine, nitrogen, phosphorus, oxygen or sulfur atom adjacent to the carbonyl carbon in the presence of a hydrolase, (b) separation of the resulting mixture of optically active amine I and amide and (c) isolation of the other enantiomer of I by cleavage of the amide.

* * * * *